United States Patent [19]

Lau et al.

[11] Patent Number: 4,782,184

[45] Date of Patent: Nov. 1, 1988

[54] METHOD FOR MAKING ETHYNYLATED AROMATIC COMPOUNDS

[75] Inventors: Kreisler S. Y. Lau, Alhambra; Thomas K. Dougherty, Rancho Palos Verdes, both of Calif.

[73] Assignee: Hughes Aircraft Company, Los Angeles, Calif.

[21] Appl. No.: 683,951

[22] Filed: Dec. 19, 1984

Related U.S. Application Data

[63] Continuation of Ser. No. 453,430, Dec. 27, 1982, abandoned.

[51] Int. Cl.$^4$ ............... C07C 87/452; C07D 215/12; C07D 213/36; C07D 207/00
[52] U.S. Cl. ..................... 564/307; 546/176; 546/264; 548/518; 549/59; 549/472; 564/308
[58] Field of Search ............ 549/74, 59, 472; 564/307, 308; 548/518; 546/176, 264

[56] References Cited

PUBLICATIONS

Roberts et al., Basic Principles of Org Chem, 1964, pp. 800-803.
Wagner et al., Synthetic Organic Chem. (1965), pp. 654-657.
Rutledge Acetylenic Compounds (1968), pp. 86-87.
Coon, Journal of Org. Chem., vol. 38, No. 25, pp. 4243-4248 (1973).

*Primary Examiner*—Alan Siegel
*Attorney, Agent, or Firm*—M. E. Lachman; A. W. Karambelas

[57] ABSTRACT

A method is disclosed for making amino-substituted ethynlated biphenyl compounds, which includes selectively nitrating symmetrically substituted biphenyl compounds, reacting the resulting nitro-substituted aromatic compound with a copper acetylide to replace the iodo substituents with ethynyl groups, and then reacting the ethynylated, nitro-substituted aromatic compound with hydrogen in the gas phase to reduce the nitro groups to amino groups. The preferred nitrating agent is nitronium trifluoromethanesulfonate, made by reaction of anhydrous nitric acid with trifluoromethanesulfonic anhydride in an anhydrous solvent.

3 Claims, No Drawings

METHOD FOR MAKING ETHYNYLATED AROMATIC COMPOUNDS

This application is a continuation of application Ser. No. 453,430, filed Dec. 27, 1982 now abandoned.

The Government has rights in this invention pursuant to Contract No. F33615-79-5101 awarded by the Department of the Air Force.

This application is a continuation of application Ser. No. 453,430, filed Dec. 27, 1982 now abandoned.

TECHNICAL FIELD

This invention relates to methods for making ethynylated aromatic compounds, and to a new method for making nitronium trifluoromethanesulfonate.

BACKGROUND OF THE INVENTION

1. Field of the Invention

Ethynylated aromatic compounds, more specifically, ethynylated biphenyl compounds, are monomers which are intermediates in the synthesis of polymers having intramolecular cyclization (IMC) capability. Such polymers include, for example, imides, quinoxalines, benzimidazoles, amides and imines. The compound 2,2'-bis(phenylethynyl)-5,5'-diaminobiphenyl is also a key intermediate in the synthesis of the 4,4'5,5'-tetramino analog which is needed to make quinoxaline and benzimidazole polymers.

Nitronium trifluoromethanesulfonate is especially effective in selectively nitrating organic compounds in high yields and with high isomeric purity. Our new method for making nitronium trifluoromethanesulfonate comprises reacting anhydrous nitric acid with trifluoromethanesulfonic anhydride in an anhydrous solvent such as dichloromethane. The resulting reagent mixture is a homogeneous solution.

2. Description of the Prior Art

A known process for preparing ethynylated biphenyl compounds such as 2,2'-bis(phenylethynyl)-5,5'-diaminobiphenyl appears in U.S. Air Force Report No. AFML-TR-76-198, entitled, "Synthesis of Polimides Curable by Intramolecular Cycloaddition," by Frederick L. Hedberg et al, dated March, 1977. Hedberg et al report an overall yield of 2,2'-bis(phenylethynyl)-5-5'-diaminobiphenyl that is less than 10% by weight of the empirically-predicted yield. And their process is both laborious and costly.

Accordingly, the need exists for a lower cost, higher yield synthesis method for making ethynylated aromatic compounds and particularly amino-substituted ethynylated biphenyl compounds.

A known process for making nitronium trifluoromethanesulfonate appears in an article entitled, "Aromatic Nitration with Nitric Acid and Trifluoromethanesulfonic Acid", by Clifford L. Coon et al, and published in the *Journal of Organic Chemistry*, Volume 38, No. 25, at pp. 4243–4248 (1973). In their process, trifluoromethanesulfonic acid reacts with anhydrous nitric acid to produce a heterogeneous mixture of nitronium trifluoromethanesulfonate and a hydronium species. These products are extremely difficult to separate from one another. Our new process produces none of the hydronium species, and our product mixture is homogeneous. In practice, our product mixture can be used in precise amounts for certain nitrations that require stringent control of stoichiometry.

SUMMARY OF THE INVENTION

This invention provides a method for making ethynylated aromatic compounds, and particularly amino-substituted ethynylated biphenyl compounds such as 2,2'-bis(phenylethynyl)-5,5'-diaminobiphenyl in high yields and at reasonable cost.

This invention also provides a novel method for making homoegeneous solutions of nitronium trifluoromethanesulfonate, in high yield and with high specificity.

The new method for making ethynylated aromatic compounds, and, in particular, amino-substituted ethynylated biphenyl compounds, begins with selective nitration of such compounds as 2,2'-diiodobiphenyl to form a first intermediate compound having nitro- and iodo-substituents. We then react this first intermediate with a copper acetylide in an ethynylation reaction, displacing the iodo-substituents and forming a second intermediate in which acetylide groups replace the iodosubstituents without displacing the nitro substituents. We then treat the second intermediate with hydrogen in the gas phase and in the presence of a noble metal-oncarbon catalyst to reduce selectively the nitro groups to amino groups.

The nitrating reagent used in this sequence is nitronium trifluoromethanesulfonate. We make this sulfonate by reacting anhydrous nitric acid with trifluoromethanesulfonic anhydride in an anhydrous solvent such as dichloromethane.

DETAILED DESCRIPTION OF THE INVENTION

In one aspect, this invention provides a new method for making an effective nitrating agent for the nitration of aromatic compounds, namely, nitronium trifluoromethanesulfonate. We make this nitrating agent by reacting trifluoromethanesulfonic anhydride with anhydrous nitric acid under anhydrous conditions, preferably in the presence of an anhydrous solvent such as dichloromethane.

To make this nitrating agent, we preferably prepare the reactants under anhydrous conditions and under an inert gas such as argon or nitrogen. Preferably, we distill trifluoromethanesulfonic anhydride under argon from a mixture of trifluromethanesulfonic acid and phosphorous pentoxide. We distill anhydrous nitric acid from a mixture of concentrated sulfuric acid and fuming nitric acid (i.e., nitric acid of 90% assay). We then react these reagents on an equimolar basis (anhydride to anhydrous nitric acid) and at a temperature in the range of about 20° C. to about 25° C. for a period of time in the range of about 10 to about 30 minutes. This process avoids the use of nitryl chloride and dinitrogen pentoxide, which require the presence of ozone, and produces a homogeneous product solution uncontaminated with hydronium trifluoromethanesulfonate.

The product mixture, which consists of a 1:1 ratio mixture of nitronium trifluoromethanesulfonate and trifluoromethanesulfonic acid, is stable and can be stored for extended periods of time under inert gases such as argon or nitrogen (preferably argon because of its higher density than air) and at temperatures in the range of about −10° C. to about +10° C. Our new method for making the new nitrating agent goes essentially to completion.

Nitronium trifluoromethanesulfonate made by our new process has many advantages in the nitration of aromatic compounds. The new nitrating agent (1) improves overall yields; (2) allows the control of delivering precise stoichiometry of nitrating agent to a substrate; (3) avoids the danger of unused reactants which may cause side reactions such as hydrolysis, oxidation and over-nitration; (4) results in high isomeric product purity; (5) avoids the use of excess strong mineral acid; and (6) simplifies overall operational procedures, both during the reaction and in the purification of product.

Ethynylated aromatic compounds, and, in particular, amino-substituted ethynylated biphenyl compounds, such as 2,2'-bis(phenylethynyl)-5,5'-diaminobiphenyl are known. However, the known methods for making these compounds are costly, low in yield, and require severe temperature and pressure conditions. Our process takes fewer steps than the known process, operates at lower temperatures, and produces higher product yields. Accordingly, our new multi-step process is lower in cost, higher in yield, simpler to operate, and readily adaptable to large-scale operation.

The first step of our new process, leading to formation of 2,2'-diiodobiphenyl, comprises reacting 1,2-dibromobenzene with n-butyllithium at −78° C. ice-acerone mixture) in the presence of an anhydrous solvent such as THF. This reaction is described in the following two articles: *Journal of Organic Chemistry*, H. Gilman, Vol. 22, page 447 (1957), and *Journal of the American Chemical Society*, S. A. Kandil, Vol. 88, page 3027 (1966).

This first step follows reaction sequence (1) below:

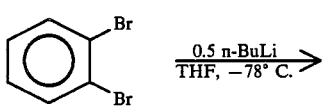

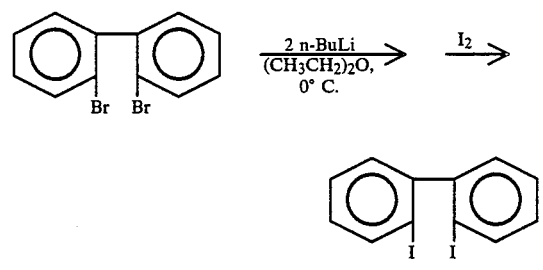

In the second step of our new process, we react 2,2'-diiodobiphenyl with nitronium trifluoromethanesulfonate, preferably at low temperatures in the range of about 0° C. to about 5° C., and in the presence of an anhydrous solvent such as dichloromethane. This selective nitration introduces one nitro group on each biphenyl ring in the meta-position with respect to the biphenyl linkage. We obtain good yields in the range of about 60% to about 70% of theoretical. The second step follows reaction sequence (2) below:

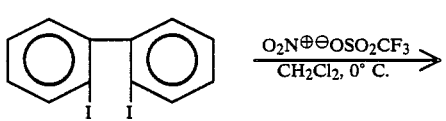

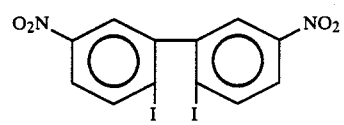

The product from the second step of our process, namely 2,2'-diiodo-5,5'-dinitrobiphenyl, is, in the third step of our process, ethynylated with a copper acetylide compound in a solvent that has a high boiling point, e.g., about 100° C. to about 120° C. These copper acetylide compounds are of the general formula CuC≡CR, where R can be an alkyl group containing one to 10 carbon atoms; an alkenyl group containing one to 10 carbon atoms; an aryl group, which can be a substituted phenyl ring or a fused aromatic nucleus such as naphthalene, anthracene, phenanthrene, pyrene, etc., or a heteroaryl group, such as furan, pyrrole, thiophene, pyridene, quinoline, etc. The ethynylation reaction forms 2,2'-bis(substituted ethynyl)-5,5'-dinitrobiphenyl compounds in yields in the range of about 55% to 80%.

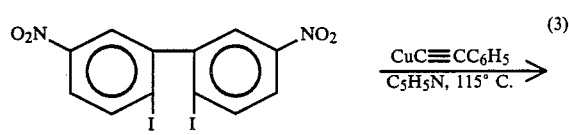

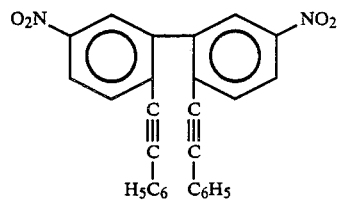

In our fourth process step, we selectively reduce the nitro groups on the ethynylated dinitrobiphenyl product by reaction with hydrogen in the gas phase, and in the presence of a catalyst comprising a noble metal and carbon, at ambient temperature, and 3–4 atmospheres of pressure. Overall yields from our four-step process are in the range of about 50% to about 90% of theoretical.

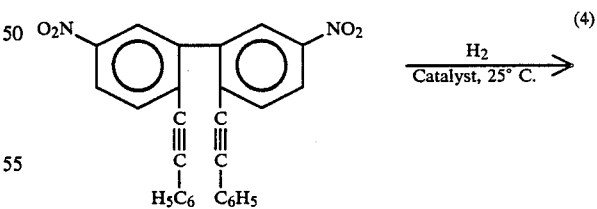

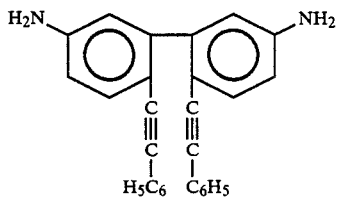

Our new process has many advantages over the process disclosed by Hedberg et al. For example, our selective nitration step takes place at a temperature in the range of about 0° C. to about 25° C. and in the presence of solvents such as dichloromethane and carbon tetrachloride, which boil at low temperatures and are readily removed from the product. The ethynylation step of our process takes place at a temperature in the range of about 25° C. to about 115° C., and in the presence of high molecular weight solvents as anhydrous pyridine, DMF or a tertiary amine. All can be removed from the reaction product by distillation or other simple separation techniques. The reduction of nitro groups into amino groups takes place at essentially ambient temperature and in conventional, low-boiling solvents that are readily removed from the final product. By contrast, prior art processes require more steps and reaction conditions which are far more severe in both temperature and pressure.

The following examples illustrate each of the new process steps.

EXAMPLE 1

Preparation of Nitronium Trifluoromethanesulfonate

Into a flame-dried, argon-purged, three-neck reaction flask, we placed 40 ml of anhydrous dichloromethane, 3.9 ml (7.1 gm, 25 mmoles) of trifluoromethanesulfonic anhydride and 1.1 ml (1.7 gm) of anhydrous nitric acid. We stirred this mixture at 25° C. for 30 minutes to produce a homogenous mixture of nitronium trifluoromethanesulfonate and trifluoromethanesulfonic acid in dichloromethane. We stored this product mixture under argon at 0° C. After storage for 10 days, under the conditions described, we analyzed the product mixture and found that no appreciable change had occurred.

EXAMPLE 2

Nitration of 2,2'-Diiodobiphenyl with Nitronium Trifluoromethanesulfonate

Into a flame-dried, argon purged, three-neck reaction flask, we placed 40 ml of a dichloromethane solution containing nitronium trifluoromethanesulfonate and trifluoromethanesulfonic acid in a molar ratio of 1:1. We cooled the solution to 0° C. and added dropwise a deaerated solution of 5.0 gm (12 mmoles) of 2,2'-diiodobiphenyl in 30 ml of anhydrous dichloromethane. We stirred these reactants for 14 hours at 25° C. and poured the resulting mixture into 500 ml of water. We separated the organic phase and washed that phase with 100 ml of saturated sodium bicarbonate solution in 100 ml of water. After drying over magnesium sulfate and removing the solvent, we obtained a pale yellow solid residue. We recrystallized this residue from an acetone/ethanol mixture and obtained 3.8 gms (7.7 mmoles; 64% yield) of pale yellow crystals having a melting point of 236°–238° C., which we raised to 239°–241° C. after further drying. We analyzed these crystals by high-performance liquid chromatography (HPLC), and found that they were 97% isomerically pure., We also analyzed the pale yellow crystals by infrared (IR) and nuclear magnetic resonance (NMR) techniques as follows, with the following results:

IR(KBr) 3100, 3070 (weak, sharp, CH), 1595, 1550 (medium sharp, aromatic C=C), 1512, 1345 (v. strong, broad, nitro groups) cm$^{-1}$.

NMR(DMSO-$d_6$) $\delta$8.15 (distorted s, 1H, aromatic $C_6$ proton) and 8.00–8.50 ppm (distorted AB quartet, 2H, aromatic $C_3$ and $C_4$ protons).

Finally, we analyzed the pale yellow crystals for elemental carbon, nitrogen and iodine contents, and compared the results we obtained to the empirical formula for 2,2'-diiodo-5,5'-dinitrobiphenyl which is $C_{12}H_6I_2N_2O_2$ and obtained these results:

Calculated: C,29.06; H,1.22; N,5.65; I,51.17. Found C,29.08; H,1.32; N,5.49; I,51.29.

NMR and HPLC analyses showed that the mother liquor product was a mixture of the 5,5'-dinitro and the 3,5'-dinitro isomers.

EXAMPLE 3

Nitration of 2,2'-Dibromobiphenyl by Nitronium Trifluoromethanesulfonate

Into a flame-dried, argon-purged, three-neck flask, we placed 50 ml of anhydrous dichloromethane, 5.8 ml (10.5 gm) of trifluoromethanesulfonic anhydride and 1.6 ml (2.2 gm) of anhydrous nitric acid, freshly distilled from sulfuric acid. We stirred this slurry at 25° C. for 30 minutes, cooled the slurry to 0° C. and then added 5.00 gm (10.0 mmoles) of 2,2'-dibromobiphenyl mixed with 20 ml of anhydrous dichloromethane. We stirred the mixture for 12 hours at 25° C. and then added 200 ml of water. We separated the organic phase, washed this phase twice with 100 ml of saturated sodium bicarbonate solution and then with water, dried the solution over magnesium sulfate and concentrated to produce 5.2 gm of pale solid yellow residue. Recrystallization of the residue from 1:3 acetone-ethanol mixture yielded 3.86 gm of pale yellow crystals having a melting point of 220°–221° C. This product yield constitutes 9.6 mmoles, or 60% of theoretical. The mother liquor yielded a second powdery solid which had a melting point of 117°–119° C.

We subjected the principal product to both infrared and NMR anaylsis as follows, and obtained the following results:

IR(KBr) 3110, 3090, 1601, 1530 (intense), 1450, 1360 (intense) cm$^{-1}$.

NMR(DMSO-$d_6$) $\delta$7.14 (s, 1H, aromatic $H_6$) and 6.90–7.30 ppm (distorted AB quartet, 2H, aromatic $H_3$ and $H_4$).

NMR analysis of the minor product supported the molecular structure of 2,2'-dibromo-3,5'-dinitrobiphenyl.

EXAMPLE 4

Preparation of 2,2'-Diiodobiphenyl from 2,2'-Dibromobiphenyl

To a solution of 8.20 gm (26.3 mmoles) of 2,2'-dibromobiphenyl [prepared by the method described in the article by H. Gilman and B. J. Gaj, reported in the "Journal of Organic Chemistry", Vol. 22, at page 447 (1957)], in 100 ml of anhydrous ether cooled under argon to a temperature in the range of 0° C. to about −5° C., we added dropwise 36 ml of a 1.6 molar hexane solution of n-butyllithium. After stirring the resulting greenish mixture at 25° C. for three hours, we cooled the solution again to 0° C. and added dropwise a solution of 13 gm of iodine in 150 ml of anhydrous ether. Initially, the brown iodine color disappeared instantaneously, but by the end of the addition, the brown iodine color persisted. We stirred the solution at 25° C. for one hour, treated the solution with aqueous sodium bisulfite, and separated the organic phase from the inorganic phase. We extracted the inorganic phase twice with 100 ml of ether, combined the two extracted phases, dried them over magnesium sulfate, and concentrated them to obtain a thick oil which crystallized upon mixing with 100 ml of methanol. We obtained a total of 7.80 gm of white crystalline product (73% of the empirically-predicted amount) having a melting point of 106°–107° C. Recrystallization from methanol raised the product's melting point to 109°–110° C. By NMR analysis, this product proved to be the desired 2,2'-diiodobiphenyl.

NMR(CDCl$_3$) $\delta$6.96–7.56 (m, 6H, aromatic C$_4$C$_5$C$_6$ protons) and 7.95 ppm (distorted d, 2H, aromatic C$_3$ proton, J$_{ortho}$=8 Hz, J$_{meta}$=2 Hz).

EXAMPLE 5

Preparation of 2,2'-Bis(phenylethynyl)5,5'-Dinitrobiphenyl

5 Into a reaction vessel, we placed a mixture of 1.986 gm (4.004 mmoles) of 2,2'-diiodo-5,5'-dinitrobiphenyl and 1.400 gm (8.509 mmoles) of copper[I] phenylacetylide in 50 ml of deaerated anhydrous pyridine. We heated this vessel under argon from a temperature of 25° C. to the reflux temperature of pyridine (115° C.) over a period of one hour and then at reflux for 16 hours. We poured the resulting dark brown mixture into 500 ml of 10% aqueous hydrochloric acid and extracted the resulting solids into 250 ml of ether. We separated the organic and aqueous phases and extracted the aqueous phase twice with 100 ml of ether. We combined the ether extracts, dried them over magnesium sulfate and concentrated them to form a solid. We recrystallized the solid from 50 ml of toluene and obtained a lightweight, bright yellow microcrystalline solid weighing 1.108 gm and having a melting point of 216°–216.5° C. Infrared, mass spectral and nuclear magnetic resonance analyses revealed that we had obtained the desired product, namely 2,2'-bis(phenylethynyl)-5,5'-dinitrobiphenyl. The yield, 2.5 mmoles, was 62.3% of theoretical.

IR, MS and NMR results on the products were as follows:

IR(KBr) 2200, 1600, 1572, 1494, very strong and broad NO$_2$ absorptions at 1515, 340, 1350 cm$^{-1}$.

MS(70eV) molecular ion at m/e 444.

NMR(CDCl$_3$) $\delta$7.30 (distorted s, 5H, C$\equiv$C-C$_6$H$_5$, 7.86(d, 1H, J=9 Hz, aromatic H3), 8.35 (d$\times$d, J's=9 Hz, 2 Hz, aromatic H4) and 8.55 ppm (d, 1H, J=2 Hz, aromatic H6).

EXAMPLE 6

Preparation of 2,2'-Bis(phenylethynyl)5,5'-Diaminobiphenyl

Into a Parr-type hydrogenation vessel, we placed a mixture of 0.700 gm (1.58 mmoles) of 2,2'-bis(phenylethynyl)-5,5'-dinitrobiphenyl, 0.225 gm of 5% ruthenium-on-charcoal and 150 ml of 2-propanol. We subjected the mixture to hydrogenation under four atmospheres of hydrogen gas for 20 hours at 25° C., filtered the resulting mixture through Celite and washed the product with chloroform. After evaporating the solvent, we obtained a lightweight yellow solid which we recrystallized from a mixture of dichloromethane and hexane. The resulting solid had a melting point of about 151° C. We subjected the product to infrared and NMR analysis as follows, and obtained the following results:

IR(KBr) 3390 (strong, broad, NH), 2220 (weak, sharp, -C$\equiv$C-), 1620, 1590, 1500 (strong, sharp, aromatic C-C) cm$^{-1}$.

NMR(CDCl$_3$) $\delta$3.68 (bs, 2H, NH$_2$), 6.68 (d$\times$d, 1H, aromatic C$_4$ proton, J$_{3,4}$=8 Hz, J$_{4,6}$=2 Hz), 7.25 (s, 5H, phenyl) and 7.50 ppm (d, 1H, aromatic C$_3$ proton, J$_{3,4}$=8 Hz).

We claim:

1. A method for making ethynylated, amino-substituted biphenyl compounds comprising:
    (a) reacting 2,2'-diiodobiphenyl with nitronium trifluoromethanesulfonate in homogeneous solution in a selected organic solvent at a temperature within the range of about zero to 5° C., to effect selective nitration in the position para to said iodo substituent to form 2,2'-diiodo-5,5'-dinitrobiphenyl;
    (b) reacting said 2,2'-diiodo-5,5'-dinitrobiphenyl with a compound of the formula CuC$\equiv$CR to form a compound of the formula 2,2'-bis(C$\equiv$CR)-5,5'-dinitrobiphenyl, where R is selected from the group consisting of an alkyl group of one to 10 carbon atoms an alkenyl group consisting one to 10 carbon atoms, an aryl group and a heteroaryl group; and
    (c) reacting the product of step (b) with hydrogen in the gas phase in the presence of a noble metal catalyst to reduce the nitro groups to amino groups.

2. The process of claim 1 wherein said nitronium trifluoromethanesulfonate is dissolved in dichloromethane.

3. The process of claim 2 wherein said nitronium trifluoromethanesulfonate is mixed with an inert solvent and trifluoromethanesulfonic acid.

* * * * *